United States Patent
Shimizu et al.

(10) Patent No.: US 10,524,652 B2
(45) Date of Patent: Jan. 7, 2020

(54) INFORMATION PROCESSING DEVICE, IMAGING SYSTEM, INFORMATION PROCESSING METHOD AND PROGRAM

(71) Applicant: TERUMO KABUSHIKI KAISHA, Shibuya-ku, Tokyo (JP)

(72) Inventors: Hijiri Shimizu, Isehara (JP); Kouichi Inoue, Odawara (JP); Junya Furuichi, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 938 days.

(21) Appl. No.: 15/075,796

(22) Filed: Mar. 21, 2016

(65) Prior Publication Data
US 2016/0199017 A1 Jul. 14, 2016

Related U.S. Application Data

(63) Continuation of application No. PCT/JP2013/005696, filed on Sep. 26, 2013.

(51) Int. Cl.
*A61B 5/00* (2006.01)
*A61B 1/313* (2006.01)

(52) U.S. Cl.
CPC .......... *A61B 1/3137* (2013.01); *A61B 5/7425* (2013.01); *A61B 5/0071* (2013.01)

(58) Field of Classification Search
CPC ....... A61B 8/12; A61B 5/0071; A61B 5/0066; A61B 5/02007; A61B 5/0073
See application file for complete search history.

(56) References Cited

U.S. PATENT DOCUMENTS

| 5,357,550 A | 10/1994 | Asahina et al. |
| 7,930,014 B2 | 4/2011 | Huennekens et al. |

(Continued)

FOREIGN PATENT DOCUMENTS

| JP | 5-064638 A | 3/1993 |
| JP | 7-155316 A | 6/1995 |

(Continued)

OTHER PUBLICATIONS

International Search Report (PCT/ISA/210) dated Oct. 29, 2013, by the Japanese Patent Office as the International Searching Authority for International Application No. PCT/JP2013/005696.

(Continued)

*Primary Examiner* — Joel Lamprecht
(74) *Attorney, Agent, or Firm* — Buchanan Ingersoll & Rooney PC

(57) ABSTRACT

In an imaging system, vascular tomographic images and vascular fluoroscopic images which each include a plurality of frames are collected. A position of an image of the probe included in each of the frames of the fluoroscopic images is acquired. The frame of the fluoroscopic image and the frame of the tomographic image which is taken at substantially the same time as the frame of the fluoroscopic image are displayed at the same time. A position of a blood vessel designated by a user is acquired from the displayed frame of the fluoroscopic image. The frame of the fluoroscopic image which includes the image of the probe at a position closer to the position of the blood vessel designated by the user is displayed at the same time as the frame of the tomographic image which is taken at substantially the same time as the frame of the fluoroscopic image.

18 Claims, 8 Drawing Sheets

(56) References Cited

U.S. PATENT DOCUMENTS

| | | | |
|---|---|---|---|
| 9,295,450 B2 * | 3/2016 | Furuichi | ................ A61B 6/12 |
| 2012/0063570 A1 | 3/2012 | Furuichi et al. | |

FOREIGN PATENT DOCUMENTS

| | | |
|---|---|---|
| JP | 10-137238 A | 5/1998 |
| JP | 2007-282974 | 11/2007 |

OTHER PUBLICATIONS

Translation of the Office Action (Notification of Reasons for Refusal) dated Dec. 5, 2016, by the Japanese Patent Office in corresponding Japanese Patent Application No. 2015-538636. (3 pages).

* cited by examiner

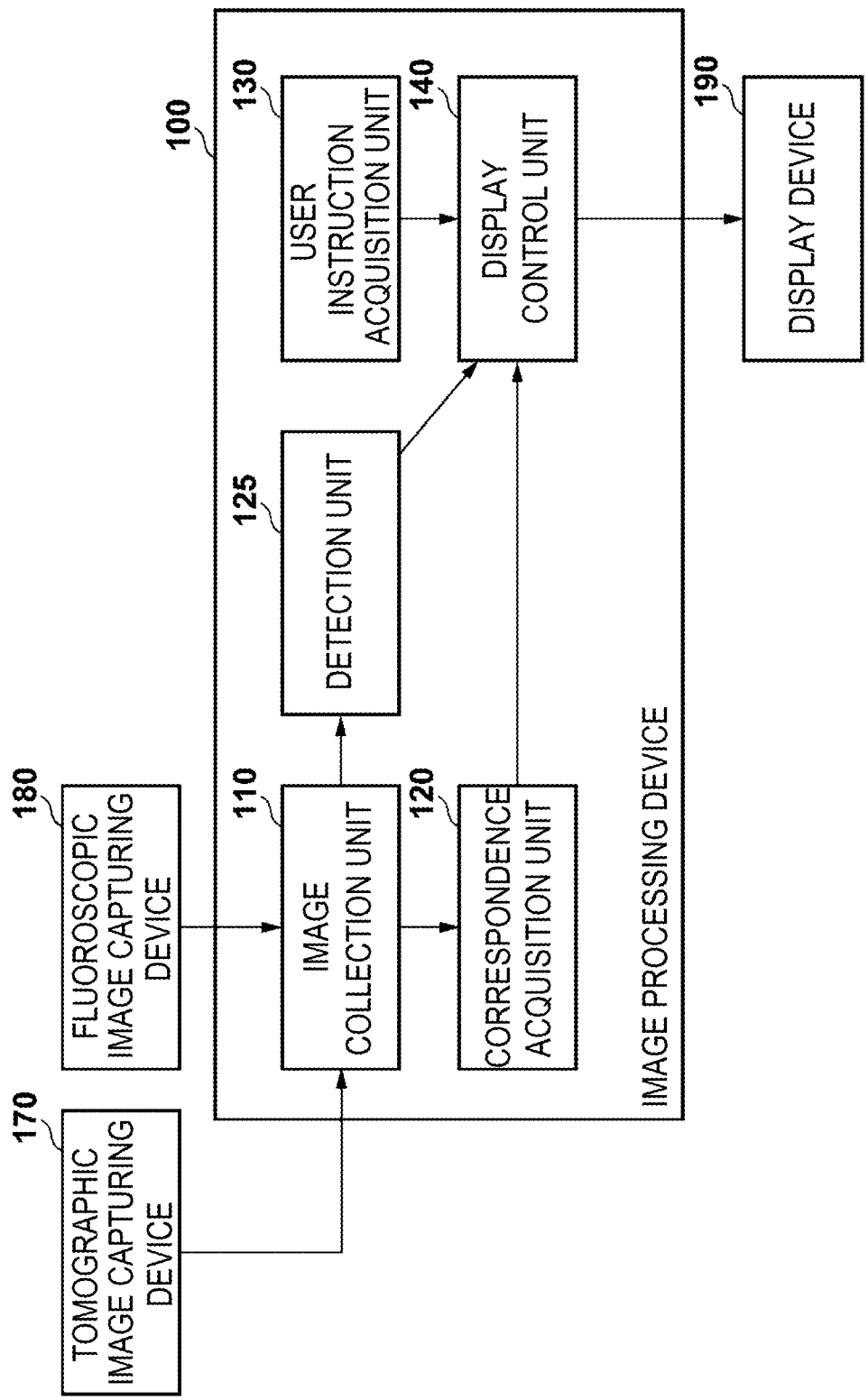
[FIG. 1]

[FIG. 2]
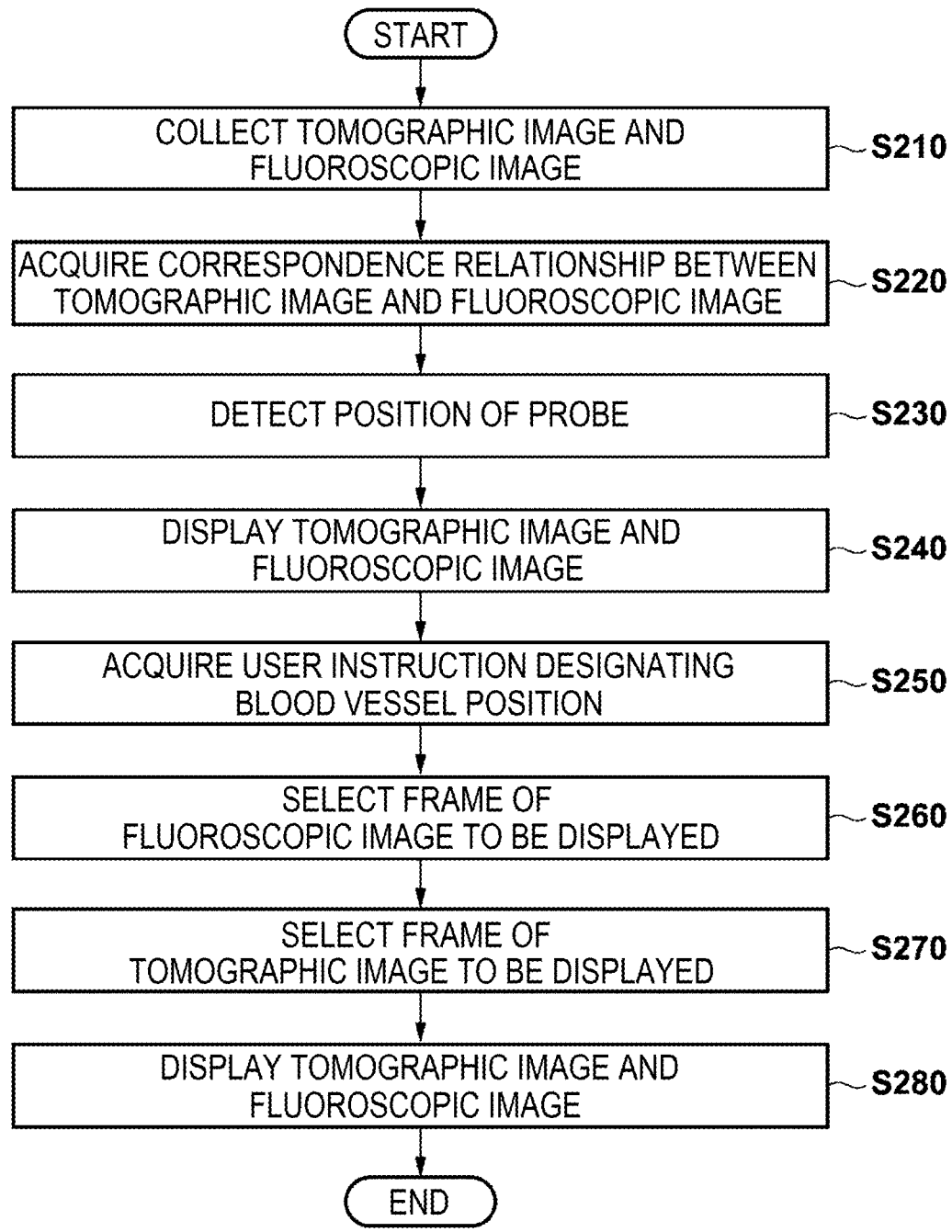

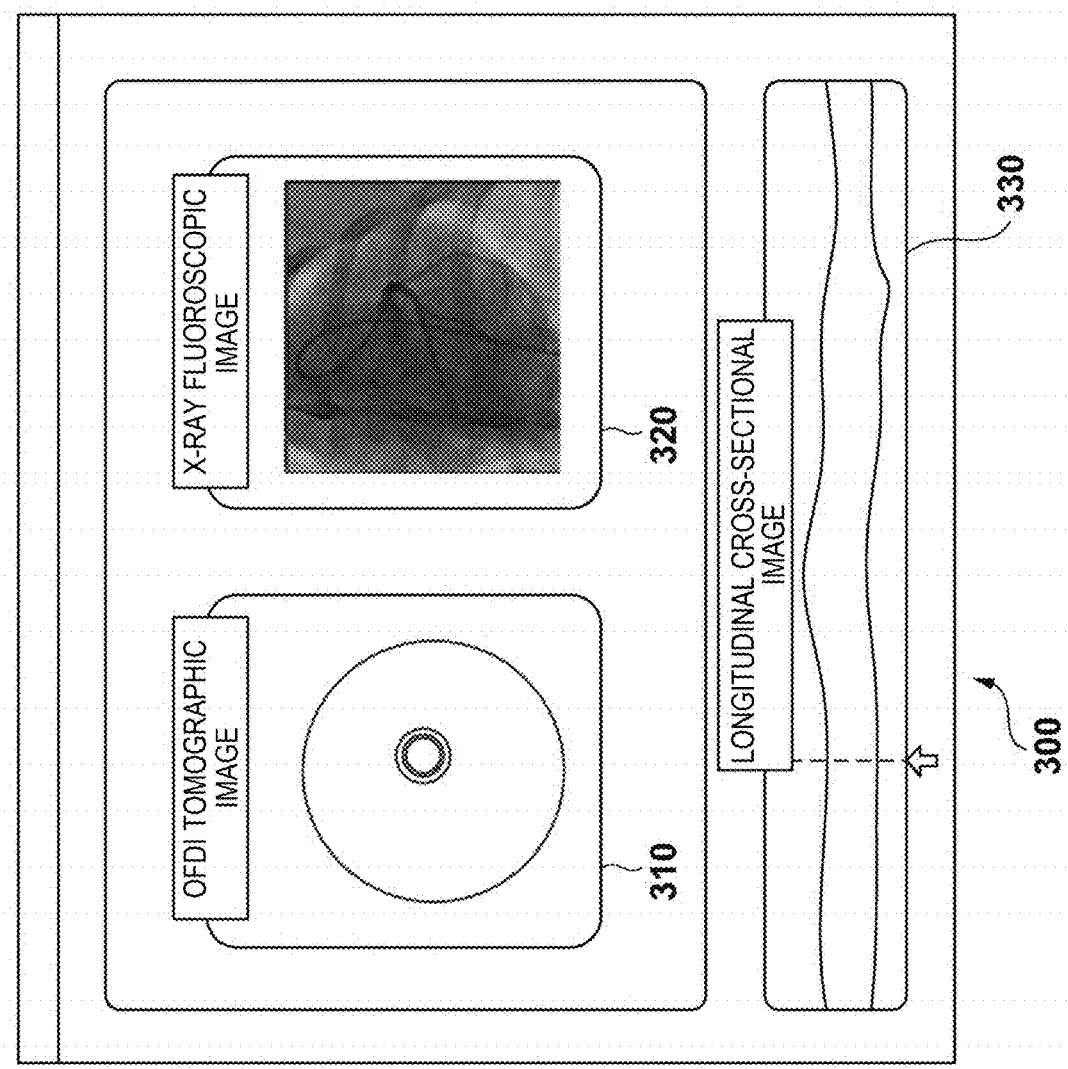
[FIG. 3]

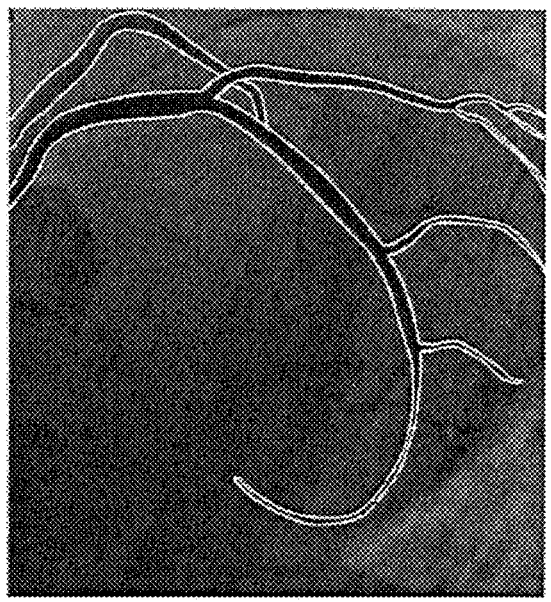
[FIG. 4A]
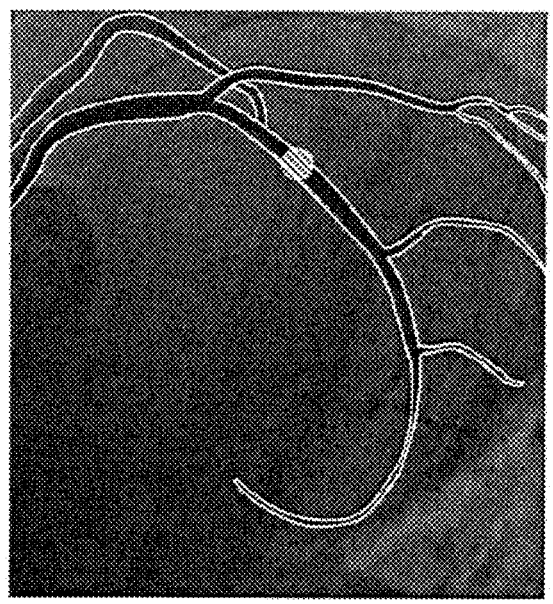
[FIG. 4B]

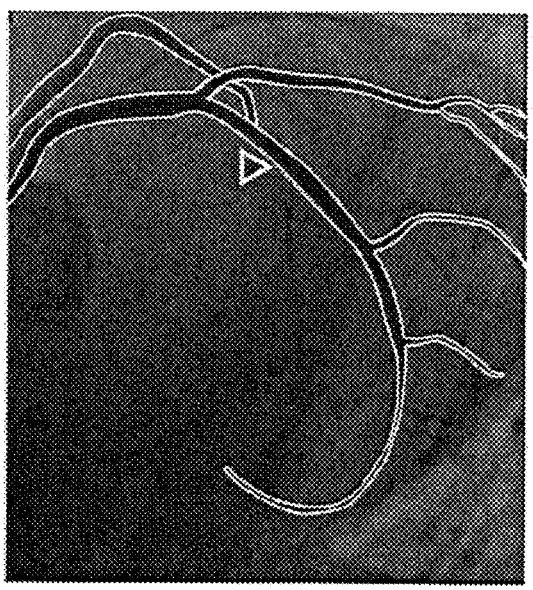
[FIG. 4C]
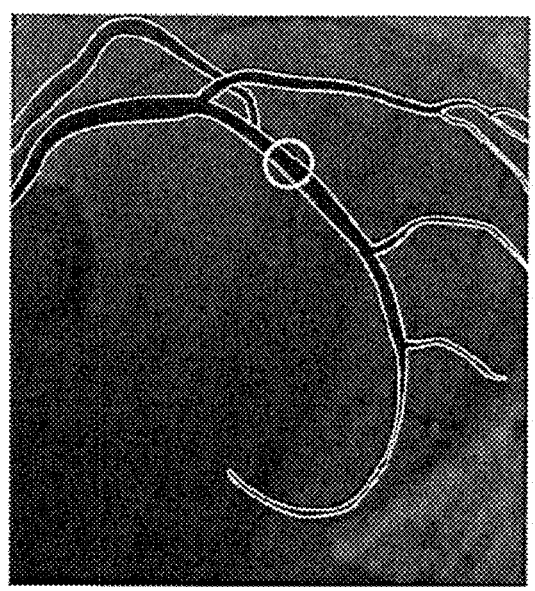
[FIG. 4D]

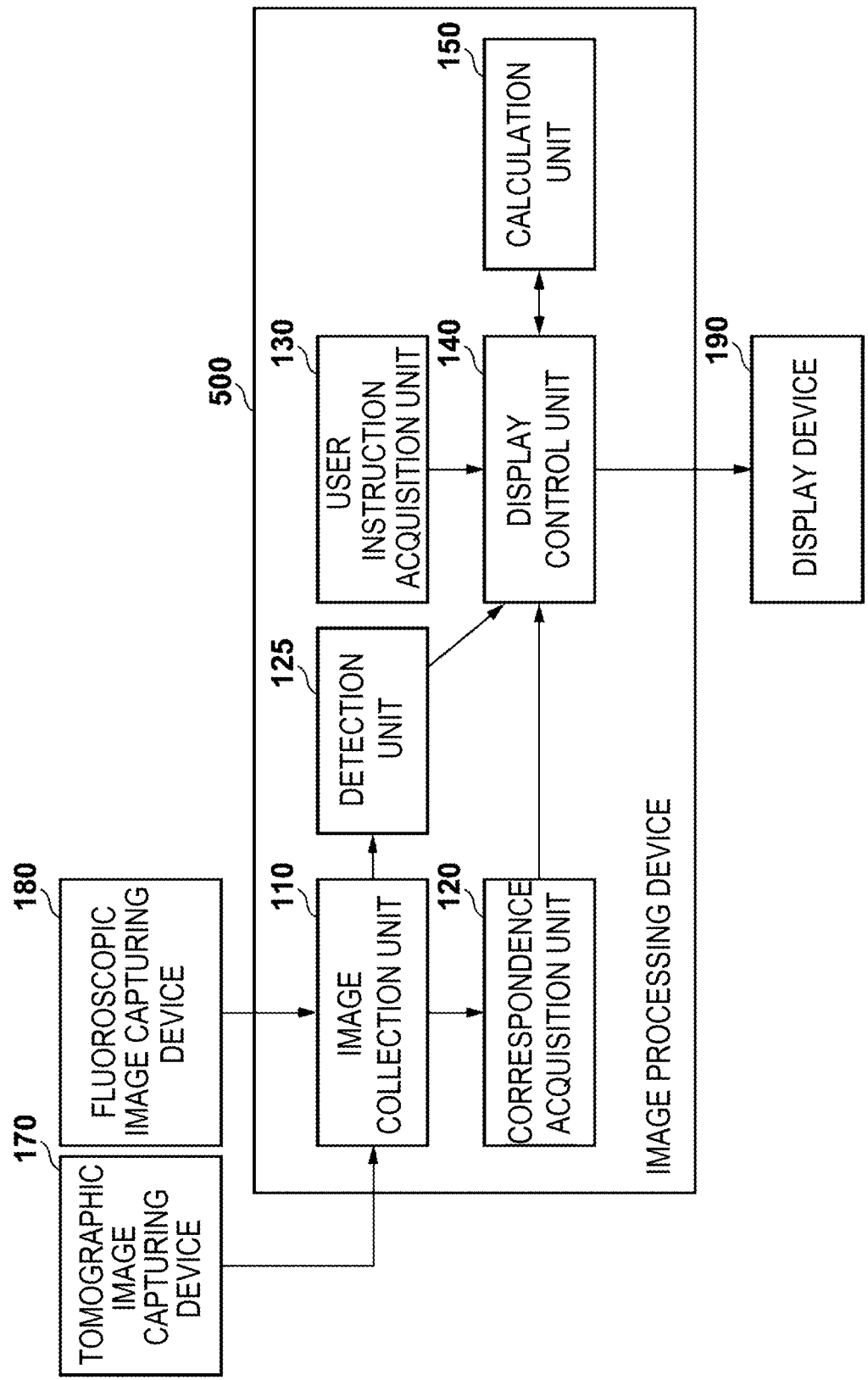

[FIG. 6]
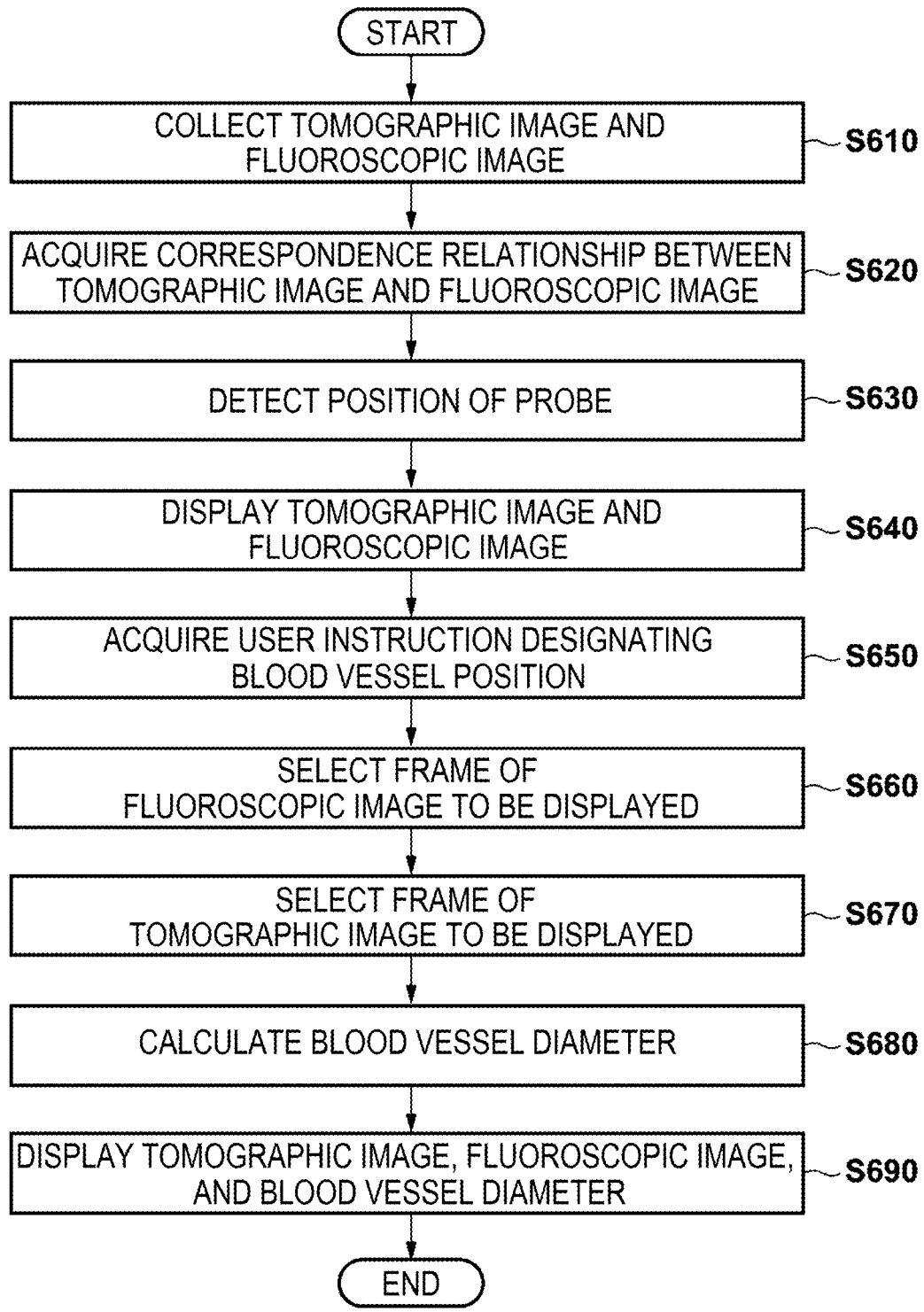

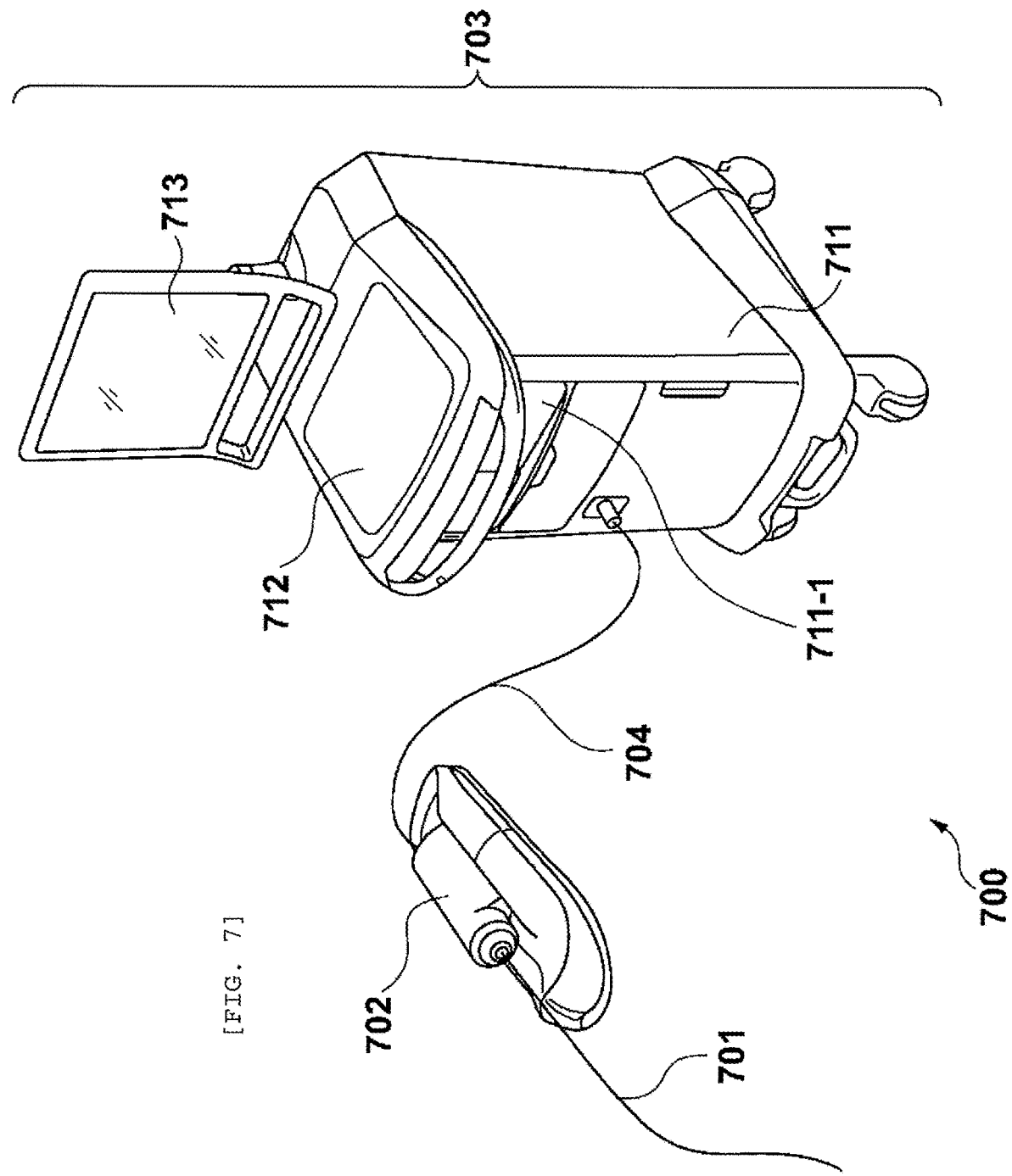
[FIG. 7]

INFORMATION PROCESSING DEVICE, IMAGING SYSTEM, INFORMATION PROCESSING METHOD AND PROGRAM

CROSS-REFERENCES TO RELATED APPLICATIONS

This application is a continuation of International Application No. PCT/JP2013/005696 filed on Sep. 26, 2013, the entire content of which is incorporated herein by reference.

TECHNICAL FIELD

The present invention relates to an information processing device, an imaging system, an information processing method, and a program, and particularly relates to displaying of an image used to perform medical diagnosis.

BACKGROUND DISCUSSION

Known medical procedures involving, for example, intravascular delivery of a balloon or a stent using a catheter are performed with reference to a diagnostic image. For example, stenosis, blockage, and the like of a blood vessel are checked by observing fluoroscopic images, such as X-ray images which are continuously captured through an angiography method during a surgical operation using the catheter. Recently, a technique of collectively checking vascular cross-sectional images obtained through an intravascular ultrasonic (IVUS) endoscope, an optical coherence tomography (OCT) apparatus, an optical frequency domain imaging (OFDI) apparatus, or the like has come into widespread use.

In such procedures, the fluoroscopic images and the cross-sectional images are used mainly to perform pre-operative diagnosis or to check the effect of post-operative medical treatment. For example, when expanding a stenosed site of a blood vessel by inserting the stent into the blood vessel, a physician will check the overall shape of the target coronary artery through the X-ray image, thereby specifying the stenosed site of the blood vessel. The physician will also use the cross-sectional image of the stenosed site to grasp the condition of a disease inside the blood vessel, thereby determining the indwelling position, the size, and the like of the stent.

As a method of displaying obtained images, for example, JP-A-2007-282974 discloses that a position of an IVUS probe inserted into a subject is displayed on an X-ray image. In addition, JP-A-H05-64638 discloses a method in which a shifted position of an ultrasonic probe is detected through an X-ray fluoroscopic image. JP-A-H05-64638 also discloses that an ultrasonic image at a predetermined position is recorded and the recorded ultrasonic image is displayed in accordance with designation of a position performed by a user.

SUMMARY

A condition of a disease can be more precisely perceived by playing and reviewing captured vascular cross-sectional images and vascular fluoroscopic images afterwards. In this case, as described above, the cross-sectional image and the fluoroscopic image captured at the same time are observed at the same time so that erroneous judgement of a practitioner can be prevented and efficiency of practice can be improved. However, even though the vascular cross-sectional images configured to include a plurality of frames and the fluoroscopic images configured to include a plurality of frames are displayed at the same time, it is not easy to search for the frame desired to be seen from the plurality of frames.

The present disclosure describes a technique in which a necessary image can be easily searched for when displaying vascular cross-sectional images and vascular fluoroscopic images which are configured to include a plurality of frames and are associated with each other.

An information processing device according to the present disclosure includes image collecting means for collecting vascular tomographic images which are taken by a probe in a blood vessel and are configured to include a plurality of frames, and vascular fluoroscopic images which are taken while the probe is being inserted into the blood vessel and are configured to include a plurality of frames; position acquiring means for acquiring a position of an image of the probe included in each of the frames of the fluoroscopic images; display controlling means for causing a display to display the frame of the fluoroscopic image at the same time as the frame of the tomographic image which is taken at substantially the same time as the frame of the fluoroscopic image; and designation acquiring means for acquiring a position of a blood vessel designated by a user from the frame of the fluoroscopic image which is displayed by the display.

The display controlling means causes the display to display the frame of the fluoroscopic image including the image of the probe at a position closer to the position of the blood vessel designated by the user at the same time as the frame of the tomographic image which is taken at substantially the same time as the frame of the fluoroscopic image.

A necessary image can be easily searched for when displaying vascular cross-sectional images and vascular fluoroscopic images which are configured to include a plurality of frames and are associated with each other.

BRIEF DESCRIPTION OF THE DRAWINGS

FIG. 1 is a diagram illustrating an example of a configuration of an information processing device according to Embodiment 1.

FIG. 2 is a flow chart illustrating an example of processing according to Embodiment 1.

FIG. 3 is a diagram illustrating a display example of Embodiment 1.

FIG. 4A is a diagram illustrating a display example of a fluoroscopic image of Embodiment 2.

FIG. 4B is a diagram illustrating another display example of the fluoroscopic image of Embodiment 2.

FIG. 4C is a diagram illustrating still another display example of the fluoroscopic image of Embodiment 2.

FIG. 4D is a diagram illustrating still another display example of the fluoroscopic image of Embodiment 2.

FIG. 5 is a diagram illustrating an example of a configuration of an information processing device according to Embodiment 3.

FIG. 6 is a flow chart illustrating an example of processing according to Embodiment 3.

FIG. 7 is a diagram illustrating an example of a configuration of an OFDI apparatus.

DETAILED DESCRIPTION

Hereinafter, embodiments of the present disclosure will be described with reference to the drawings. In the drawings, the same reference numerals and signs will be applied to the same or similar configurations.

Hereinafter, an information processing device according to Embodiment 1 will be described. FIG. 1 is a block diagram illustrating an example of a configuration of an information processing device 100 according to the present embodiment, embodied, for example, as a CPU. The information processing device 100 according to the present embodiment includes an image collection unit 110, a correspondence acquisition unit 120, a detection unit 125, a user instruction acquisition unit 130, and a display control unit 140, embodied, for example, as software modules executed by the CPU corresponding to the information processing device 100. In addition, the information processing device 100 is connected to a display device 190.

The image collection unit 110 collects vascular tomographic images and vascular fluoroscopic images. The type of the vascular tomographic image is not particularly limited. However, for example, the type thereof can be an ultrasonic tomographic image, an optical tomographic image, or the like. In the present embodiment, the tomographic images collected by the image collection unit 110 are taken by a probe in a blood vessel. In addition, in the present embodiment, the fluoroscopic images collected by the image collection unit 110 are taken while the vascular tomographic images are taken by the probe in the blood vessel. The image collection unit 110 is connected to a tomographic image capturing device 170 and a fluoroscopic image capturing device 180. The tomographic images and the fluoroscopic images are collected through the devices. The devices normally acquire transverse cross-sectional images in a vascular diameter direction (cross-sectional images of a blood vessel in a transverse direction). However, the devices can also obtain longitudinal cross-sectional images in a vascular length direction (cross-sectional images of a blood vessel in an axial direction) from the transverse cross-sectional images.

The ultrasonic tomographic image can be acquired, for example, through an IntraVascular UltraSound (IVUS) diagnostic apparatus or the like. In addition, the optical tomographic image can be acquired, for example, through an optical coherence tomography (OCT) apparatus, an optical frequency domain imaging (OFDI) apparatus, or the like. In the following description, the image collection unit 110 is considered to collect the optical tomographic images which are obtained by using the OFDI apparatus.

In the present embodiment, the tomographic images collected by the image collection unit 110 are configured to include a plurality of frames. For example, the tomographic images configured to include the plurality of frames can be obtained by continuously taking the tomographic images while inserting an optical probe of the OFDI apparatus into a blood vessel such as the coronary artery via a catheter and pulling the optical probe.

In addition, the type of the vascular fluoroscopic image is also not particularly limited. However, for example, the type thereof can be an X-ray image which is taken by using a contrast agent through an angiography method. In other words, the fluoroscopic images configured to include the plurality of frames can be obtained by continuously capturing the X-ray images while pulling the optical probe of the OFDI apparatus. The image collection unit 110 in this embodiment therefore corresponds to an example of image collecting means for collecting vascular tomographic images which are taken by a probe inserted into a blood vessel and are configured to include a plurality of frames, and vascular fluoroscopic images which are taken while the probe is being inserted into the blood vessel and are configured to include a plurality of frames.

Hereinafter, the OFDI apparatus will be simply described with reference to FIG. 7. An OFDI apparatus 700 includes a probe unit 701, a scanner and pull-back unit 702, and an operation control apparatus 703. The scanner and pull-back unit 702 and the operation control apparatus 703 are connected to each other through a signal line 704 so that various signals can be transmitted.

The probe unit 701 is directly inserted into a blood vessel and continuously transmits sent light (measurement light) to the inside of the blood vessel. An imaging core including an optical transceiver which continuously receives reflected light from the inside of the blood vessel is interpolated into the probe unit 701. The OFDI apparatus 700 measures a state of the inside of the blood vessel by using the imaging core.

The probe unit 701 is detachably attached to the scanner and pull-back unit 702. Operations of the imaging core interpolated into the probe unit 701 are regulated inside the blood vessel in the axial direction and a rotation direction by driving a built-in motor. In addition, the scanner and pull-back unit 702 acquires the reflected light received by the optical transceiver and transmits the light to the operation control apparatus 703.

The operation control apparatus 703 has a function of inputting various setting values during measurement, and a function of processing data obtained through the measurement and displaying the cross-sectional images (the transverse cross-sectional images and the longitudinal cross-sectional images) inside the blood vessel.

The operation control apparatus 703 includes a main body control unit 711, embodied as a processor which generates optical cross-sectional images by processing line data generated based on the reflected light which is obtained through the measurement.

A printing and storage unit 711-1, which can be a printer and a DVD recorder in the embodiment, prints a processed result of the main body control unit 711 and stores the processed result as data. A user inputs various types of setting values and instructions via the an operation panel 712. An LCD monitor 713 serves as a display device, which displays the cross-sectional image generated in the main body control unit 711.

The information processing device 100 according to the present embodiment collects the tomographic images and the fluoroscopic images from the image capturing devices for the tomographic image and the fluoroscopic image. However, the information processing device 100 according to the present embodiment may be embedded into the image capturing device for the tomographic image or the fluoroscopic image. For example, the main body control unit 711 illustrated in FIG. 7 may include each of the configuration elements of the information processing device 100 illustrated in FIG. 1. In this case, the display control unit 140 can control displaying of the LCD monitor 713, and the user instruction acquisition unit 130 can acquire user instructions through the operation panel 712. In addition, an imaging system including the image capturing device which captures the tomographic images and the image capturing device which captures the fluoroscopic images may also include the information processing device 100 according to the present embodiment.

The correspondence acquisition unit 120 acquires a correspondence relationship between each of the frames configuring the fluoroscopic images and each of the frames configuring the tomographic images. Specifically, the correspondence acquisition unit 120 determines the frame of the tomographic image which is taken at substantially the same time as the frame of the fluoroscopic image regarding each of the frames configuring the fluoroscopic images. A method of acquiring the correspondence relationship is not particularly limited. The frame of the tomographic image which is taken at substantially the same time as the frame of the fluoroscopic image can be a frame of the tomographic image which is taken within a predetermined time range from a taking time of the frame of the fluoroscopic image. When there is no frame of the tomographic image which is taken at substantially the same time as the frame configuring the fluoroscopic image, the correspondence acquisition unit 120 can record that no corresponding frame of the tomographic image is present. The frame of the tomographic image which is taken at substantially the same time as the frame of the fluoroscopic image may be a frame of the tomographic image which is taken in a predetermined time interval including a time point taking the frame of the fluoroscopic image. Although a decision method for the predetermined time interval is not restricted, for example, an imaging sampling interval can be used. An imaging sampling rate, i.e. frame rate, of capturing the tomographic images may be different from an imaging sampling rate, i.e. frame rate, of capturing the fluoroscopic images. For example, the frame rate of capturing the tomographic images is 100-200 frames per second, and the frame rate of capturing the fluoroscopic images is 15-30 frames per second. Then, the imaging sampling interval of the frame capturing of lower frame rate can be used.

For example, the correspondence acquisition unit 120 can acquire the correspondence relationship by performing image processing with respect to the tomographic image and the fluoroscopic image. As an example thereof, the correspondence acquisition unit 120 detects a position of the probe from the fluoroscopic image and calculates a length of insertion of the probe, thereby being able to determine the tomographic image corresponding to the calculated length of the probe. In addition, the correspondence acquisition unit 120 can also acquire the correspondence relationship in accordance with a geometric feature, e.g. bifurcating position, of a blood vessel detected from the fluoroscopic image and the geometric feature (bifurcating position) of the blood vessel detected from the tomographic image. Moreover, the correspondence acquisition unit 120 can acquire the correspondence relationship with reference to a time-stamp applied to each of the frames configuring the fluoroscopic images and a time-stamp applied to each of the frames configuring the tomographic images. As another alternative method, the correspondence acquisition unit 120 can acquire the correspondence relationship with reference to a frame rate of the fluoroscopic image and a frame rate of the tomographic image. The correspondence acquisition unit 120 in this embodiment therefore corresponds to an example of correspondence acquiring means for acquiring information indicating the frame of the tomographic image which is taken at substantially the same time as the frame of the fluoroscopic image regarding each of the frames of the fluoroscopic images.

The detection unit 125 detects a position of an image of the probe included in each of the frames configuring the fluoroscopic images. The detection unit 125 in this embodiment therefore corresponds to an example of position identifying means for identifying a position of an image of the probe in each of the frames of the fluoroscopic images. For example, the position of the probe can be detected from the frame of the fluoroscopic image by attaching a member having high X-ray absorption characteristics to a distal end of the optical probe of the OFDI apparatus. In this case, the position of the probe is detected as a portion having higher absorption characteristics in the blood vessel. However, the information processing device 100 does not necessarily include the detection unit 125. For example, the image collection unit 110 may collect information indicating the position of the probe in each of the frames configuring the fluoroscopic images together with the fluoroscopic images.

The user instruction acquisition unit 130 acquires user instructions designating a position of a blood vessel. The user instructions are given in a frame of the fluoroscopic image which is displayed on the display device 190. For example, a user can designate a blood vessel at a predetermined position in the fluoroscopic image which is displayed by using an input device (not illustrated) such as a mouse. In this case, the user instruction acquisition unit 130 acquires a designated position of a blood vessel. When the display device 190 includes a touch screen, the user may input designation of a position via the touch screen. The user instruction acquisition unit 130 in this embodiment therefore corresponds to an example of designation acquiring means for acquiring information of a position of a blood vessel designated by a user from the frame of the fluoroscopic image which is displayed by the display.

The display control unit 140 causes the display device 190 to display the tomographic image and the fluoroscopic image. In the present embodiment, in order to allow a practitioner (an operator) to make more precise determination, the display control unit 140 causes the display device 190 to display the frame of the tomographic image at the same time as the frame of the fluoroscopic image which is captured at substantially the same time as the frame of the tomographic image. The display control unit 140 in this embodiment therefore corresponds to an example of display controlling means for causing a display to display the frame of the fluoroscopic image at the same time as the frame of the tomographic image which is taken at substantially the same time as the frame of the fluoroscopic image.

In addition, the display control unit 140 changes the frame to be displayed by the display device 190 in accordance with the user instructions acquired by the user instruction acquisition unit 130. In the present embodiment, the display control unit 140 causes the display device 190 to display the transverse cross-sectional image. However, the display control unit 140 can cause the display device 190 to additionally display the longitudinal cross-sectional image. Specified processing of the display control unit 140 will be described later.

Subsequently, an example of processing performed by the information processing device 100 according to the present embodiment will be described with reference to the flow chart in FIG. 2.

In Step S210, as described above, the image collection unit 110 collects the vascular tomographic images and the vascular fluoroscopic images. In Step S220, as described above, the correspondence acquisition unit 120 acquires the correspondence relationship between the vascular fluoroscopic image and the vascular tomographic image. In Step S230, the detection unit 125 detects the position of the probe from each of the frames configuring the fluoroscopic images, as described above. For example, when the number of the symmetrical frames of the fluoroscopic image is referred to as k, and the coordinates of the detected position of the probe are referred to as (x, y), the detection unit 125 records multiple combinations of (x, y, k). The detection unit 125 in this embodiment therefore corresponds to an example of position identifying means which identifies the position of the image of the probe by detecting the image of the probe from each of the frames of the fluoroscopic images.

In Step S240, the display control unit 140 causes the display device 190 to display one frame among the fluoroscopic images and a corresponding frame of the tomographic image at the same time. A method of selecting the frame to be displayed in Step S240 is not particularly limited. For example, the display control unit 140 may display a first frame among the frames configuring the fluoroscopic images. When there is no frame of the tomographic image corresponding to the selected frame of the fluoroscopic image, the display control unit 140 does not have to cause the tomographic image to be displayed. As an alternative method, when there is no frame of the tomographic image corresponding to the selected frame of the fluoroscopic image, the display control unit 140 may cause the frame of the tomographic image which is taken at a time closest to the taking time of the frame of the fluoroscopic image to be displayed.

In Step S250, the user instruction acquisition unit 130 acquires the user instructions designating a position of a blood vessel, as described above. The position acquired by the user instruction acquisition unit 130 in Step S250 is referred to as $(x_u, y_u)$ hereinafter.

In Step S260, the display control unit 140 determines the frame of the fluoroscopic image corresponding to the position of the blood vessel which is designated through the user instructions of the user instruction acquisition unit 130, as the frame to be displayed. As a specific example, the display control unit 140 can select the frame of the fluoroscopic image including the image of the probe at a position closer to the position of the blood vessel which is designated through the user instructions. For example, the display control unit 140 can select a combination of $(x_0, y_0, k_0)$ having a shorter distance between the coordinates $(x_0, y_0)$ and the coordinates $(x_u, y_u)$ acquired in Step S250, among the multiple combinations of $(x, y, k)$ recorded in Step S230. Specifically, the display control unit 140 can select $(x_0, y_0, k_0)$ so as to cause the distance between the coordinates $(x_0, y_0)$ and the coordinates $(x_u, y_u)$ to be the shortest. A frame $k_0$ which is determined in such a manner becomes the frame of the fluoroscopic image to be displayed. The frame which is selected in such a manner corresponds to a frame which is captured while the probe is present in the vicinity of the position of the blood vessel which is designated through the user instructions. Note that, the origin for regulating the coordinates may be set based on a characteristic site having geometric feature (e.g. bifurcated point or the like) of the blood vessel in the fluoroscopic image and the origin may be varied for each of the frames.

In Step S270, the display control unit 140 determines a frame $k_1$ of the tomographic image corresponding to a frame $k_0$ of the fluoroscopic image in accordance with the correspondence relationship acquired in Step S220. In Step S280, the display control unit 140 causes the display device 190 to display the frame $k_0$ of the fluoroscopic image determined in Step S260 and the frame $k_1$ of the tomographic image determined in Step S270. FIG. 3 illustrates a display example of Step S280. A display example 300 illustrated in FIG. 3 includes a frame 310 of the tomographic image and a frame 320 of the fluoroscopic image. As illustrated in FIG. 3, the display example 300 may additionally include the longitudinal cross-sectional image, and a position corresponding to the position of the blood vessel designated by the user may be indicated on the longitudinal cross-sectional image. The display control unit 140 in this embodiment therefore corresponds to an example of display controlling means which causes the display to display the frame of the fluoroscopic image including the image of the probe at a position closer to the position of the blood vessel designated by the user at the same time as the frame of the tomographic image which is taken at substantially the same time as the frame of the fluoroscopic image.

When there is no frame of the tomographic image corresponding to the selected frame of the fluoroscopic image, the display control unit 140 does not have to cause the tomographic image to be displayed. As an alternative method, when there is no frame of the tomographic image corresponding to the selected frame of the fluoroscopic image, the display control unit 140 may cause the frame of the tomographic image which is taken at a time closest to the taking time of the frame of the fluoroscopic image to be displayed. Moreover, when there is no frame of the tomographic image corresponding to the selected frame of the fluoroscopic image, processing may return to Step S250, thereby acquiring the user instructions again. In this case, the display control unit 140 can notify the user of the absence of the corresponding tomographic image via the display device 190.

According to the present embodiment described above, the frame of the fluoroscopic image which is taken while the probe is present at a position designated in the fluoroscopic image can be displayed at the same time as the frame of the cross-sectional image when displaying the vascular cross-sectional images and the vascular fluoroscopic images which are configured to include the plurality of frames and are associated with each other.

In Step S260 of the present embodiment, the display control unit 140 has selected $(x_0, y_0, k_0)$ so as to cause the distance between the coordinates $(x_0, y_0)$ and the coordinates $(x_u, y_u)$ to be the shortest. In this case, the display control unit 140 may additionally determine whether or not the distance between the coordinates $(x_0, y_0)$ and the coordinates $(x_u, y_u)$ is equal to or less than a predetermined threshold value. When the distance exceeds the predetermined threshold value, processing may return to Step S250 without displaying the selected frame, thereby acquiring the user instructions again. In this case, the display control unit 140 can notify the user of the absence of the corresponding fluoroscopic image and tomographic image via the display device 190. The display control unit 140 in this embodiment therefore corresponds to an example of display controlling means for causing the frame of the fluoroscopic image including the image of the probe at the position closer to the position of the blood vessel designated by the user to be displayed when a distance between the position of the image of the probe included in the frame of the fluoroscopic image and the position of the blood vessel designated by the user is equal to or less than a predetermined threshold value Since blood vessels can move due to physical activity, the position of a blood vessel in each of the frames of the fluoroscopic images may vary. Particularly, the coronary artery significantly moves in accordance with cardiac beats. In such a case, in response to the position of the blood vessel in the fluoroscopic image, the position of the probe detected in Step S230 and the user designated position on an image acquired in Step S250 can be corrected.

As a specific example, the coordinates in the fluoroscopic image designated by the user can be converted into relative coordinates with respect to a vascular image. For example, the user instruction acquisition unit 130 can detect a geometric feature point of a blood vessel from the frame of the fluoroscopic image. For example, the geometric feature point is a bifurcated point or the like of a blood vessel. The geometric feature point may be automatically detected by the user instruction acquisition unit 130 or may be input by an operator. The user instruction acquisition unit 130 can convert the coordinates in the fluoroscopic image designated by the user into a relative coordinate system based on the detected geometric feature point. Similarly, the detection unit 125 can also convert the detected position of the probe into the relative coordinate system based on the detected geometric feature point. In this case, processing of selecting the frame of the fluoroscopic image in Step S260 can be performed by using the relative coordinates.

As an alternative method, there is a method in which frames of image are grouped by cardiac cycle to at least two groups having at least one frame. As one of the methods, an image captured during either one of a systolic phase or a diastolic phase is not subjected to processing and an image taken during the other one thereof is subjected to processing. Specifically, in Step S260, the display control unit 140 can select the frame of the fluoroscopic image corresponding to the position of the blood vessel complying with the user instructions, that is, an image taken during the diastolic phase as the frame to be displayed. According to the method, an image during the systolic phase in which blood vessels significantly move is excluded from the selection target, and thus, it is possible to prevent an unintentional image from being displayed. In addition, the user instruction acquisition unit 130 can be configured to acquire the position of the blood vessel designated in the fluoroscopic image of the heart during the diastolic phase and not to acquire the position of the blood vessel designated in the fluoroscopic image of the heart during the systolic phase.

As another alternative method, an image captured during the systolic phase and an image taken during the diastolic phase can be independently handled. In other words, when the user instruction acquisition unit 130 acquires the position of the blood vessel designated in the fluoroscopic image of the heart during the diastolic phase, the display control unit 140 can select an image taken during the diastolic phase as the frame to be displayed. In contrast, when the user instruction acquisition unit 130 acquires the position of the blood vessel designated in the fluoroscopic image of the heart during the systolic phase, the display control unit 140 can select an image taken during the systolic phase as the frame to be displayed. In such a case, the detection unit 125 can separately record the combinations of (x, y, k) for each of the fluoroscopic image during the diastolic phase and the fluoroscopic image during the systolic phase.

Hereinafter, an information processing device according to Embodiment 2 will be described. The information processing device 100 according to the present embodiment has a configuration similar to that of Embodiment 1. In addition, processing according to the present embodiment is also similar to that of Embodiment 1. However, processing of Steps S240 and S280 is different from that of Embodiment 1. Hereinafter, description of a configuration similar to that of Embodiment 1 will be omitted.

Specifically, in Step S240, the display control unit 140 causes the display device 190 to additionally display the information indicating the position of the image of the probe detected from the fluoroscopic image when the display device 190 displays one frame among the fluoroscopic images and the corresponding frame of the tomographic image at the same time. For example, the display control unit 140 can cause a marker indicating the position of the probe to be displayed so as to be superimposed on the fluoroscopic image. The position of the probe is detected in Step S230. In other words, in a case of displaying the frame $k_0$ when the combination of $(x_0, y_0, k_0)$ is recorded, the marker is displayed so as to be superimposed at the coordinates $(x_0, y_0)$ in the fluoroscopic image. FIGS. 4B, 4C, and 4D illustrate examples in each of which the marker is displayed so as to be superimposed on the fluoroscopic image illustrated in FIG. 4A. For example, as illustrated in FIG. 4B, the color of the position of the probe can be changed, that is, a marker having a predetermined color can be superimposed on the position of the probe. In addition, as illustrated in FIG. 4C, for example, a triangular marker can be displayed so as to be superimposed in the vicinity of the position of the probe. Moreover, as illustrated in FIG. 4D, for example, a circular marker surrounding the position of the probe can be displayed so as to be superimposed thereon.

In Step S280 as well, the display control unit 140 causes the marker indicating the position of the probe detected from the fluoroscopic image to be displayed so as to be superimposed on the fluoroscopic image, when the display device 190 displays the frame $k_0$ of the fluoroscopic image and the frame $k_1$ of the tomographic image. Displaying of the marker can be performed similar to Step S240. The display control unit 140 in this embodiment therefore corresponds to an example of display controlling means for causing the display to display information indicating the position of the image of the probe included in the frame of the fluoroscopic image in addition to the frame of the fluoroscopic image.

According to the present embodiment described above, the position of the blood vessel can be easily checked in the fluoroscopic image corresponding to the cross-sectional image when displaying the vascular cross-sectional image and the vascular fluoroscopic image which are configured to include the plurality of frames and are associated with each other.

Hereinafter, an information processing device according to Embodiment 3 will be described. FIG. 5 is a block diagram illustrating an example of a configuration of an information processing device 500 according to the present embodiment. The information processing device 500 according to the present embodiment has a configuration similar to that of Embodiment 1. However, the information processing device 500 additionally includes a calculation unit 150. Hereinafter, description of a configuration similar to that of Embodiment 1 will be omitted. In the present embodiment, the calculation unit 150 acquires vascular information at the position of the blood vessel designated by the user. In the present embodiment, a vascular diameter is calculated as the vascular information.

Subsequently, processing according to the present embodiment will be described with reference to the flow chart illustrated in FIG. 6. Steps S610 to S670 are similar to Steps S210 to S270, and description thereof will be omitted. In Step S680, the calculation unit 150 calculates the vascular diameter at the position of the blood vessel indicated through the user instructions acquired by the user instruction acquisition unit 130 in Step S650. Specifically, the calculation unit 150 extracts an inner wall portion of the blood vessel from the frame $k_1$ of the tomographic image determined by the display control unit 140 in Step S270. Then, the calculation unit 150 calculates the extracted diameter of the inner wall portion of the blood vessel as the vascular diameter. In this case, the calculation unit 150 can calculate the vascular diameter with reference to resolution information which is collected by the image collection unit 110 and is applied to the tomographic image. The calculation unit 150 in this embodiment therefore corresponds to an example of vascular information acquiring means for acquiring acquires a vascular diameter with reference to the frame of the tomographic image at the position of the blood vessel designated by the user as the vascular information.

In Step S690, the display control unit 140 causes the information indicating the vascular diameter calculated by the calculation unit 150 in Step S680 to be displayed, when the display device 190 displays the frame $k_0$ of the fluoroscopic image and the frame $k_1$ of the tomographic image. For example, the display control unit 140 can cause a numerical value of the vascular diameter to be displayed so as to be superimposed in the vicinity of the position of the probe detected from the fluoroscopic image. The display control unit 140 in this embodiment therefore corresponds to an example of display controlling means for causing the display to display the vascular information.

According to the present embodiment described above, the vascular diameter at the position designated in the fluoroscopic image can be easy to know. In the present embodiment, the vascular diameter at the designated position is displayed. However, the information to be displayed is not limited thereto. In other words, arbitrary information which can be obtained from the tomographic image corresponding to the designated position can be displayed. For example, a vascular lumen area at the designated position may be displayed.

In addition, in the present embodiment, the fluoroscopic image and the tomographic image corresponding to the position designated in the fluoroscopic image are displayed together with the vascular diameter. However, displaying thereof may be independently performed. For example, when the user inputs instructions indicating that the vascular diameter is to be displayed, after displaying the fluoroscopic image and the tomographic image corresponding to the position designated in the fluoroscopic image, the vascular diameter corresponding to the position may be calculated and displayed.

Hereinafter, an information processing device according to Embodiment 4 will be described. The information processing device 500 according to the present embodiment has a configuration similar to that of Embodiment 3. In addition, processing according to the present embodiment is also similar to that of Embodiment 3. However, processing of Steps S650 to S690 is different from that of Embodiment 3. Hereinafter, description of a configuration similar to that of Embodiment 3 will be omitted. In the present embodiment, the calculation unit 150 calculates a vascular length between two positions in the blood vessel designated by the user, as the vascular information.

In Step S650, the user instruction acquisition unit 130 acquires the user instructions designating the two positions in the blood vessel. In Step S660, the display control unit 140 selects the corresponding frame of the fluoroscopic image for each of the two positions in the blood vessel, similar to Embodiment 3. In Step S670, the display control unit 140 selects the corresponding frame of the tomographic image for each of the two frames of the fluoroscopic images selected in Step S660 similar to Embodiment 3.

In Step S680, the calculation unit 150 calculates the vascular length between the two positions in the blood vessel complying with the user instructions acquired in Step S650. For example, the calculation unit 150 can calculate the vascular length for each of the frames of the tomographic images acquired in Step S610, with reference to information indicating the length of insertion of the probe with respect to a fiducial position. The image collection unit 110 can collect such information together with the tomographic image through the tomographic image capturing device 170. More specifically, the calculation unit 150 can calculate a difference between the length of insertion corresponding to the frame of the tomographic image which corresponds to a first position of the blood vessel in the two positions in the blood vessel and the length of insertion corresponding to the frames of the tomographic images which corresponds to a second position of the blood vessel in the two positions in the blood vessel, as the vascular length. The calculation unit 150 in this embodiment therefore corresponds to an example of vascular information acquiring means for acquiring a vascular length between two positions in the blood vessel designated by the user as the vascular information.

However, the method of calculating the vascular length is not limited to this method. For example, when the tomographic images are taken in predetermined intervals, the vascular length can be calculated based on the difference between a frame number of the tomographic image corresponding to the first position of the blood vessel and another frame number of the tomographic image corresponding to the second position of the blood vessel. In this case, the image collection unit 110 can collect the information indicating the length in the vascular diameter direction between continuous positions where the frames are captured, through the tomographic image capturing device 170 together with the tomographic image.

In Step S690, the display control unit 140 causes the information indicating the vascular length calculated by the calculation unit 150 in Step S680 to be displayed, when the display device 190 displays the frame of the fluoroscopic image and the frame of the tomographic image. For example, the display control unit 140 can cause the numerical value of the vascular length to be displayed so as to be superimposed in the vicinity of the position of the probe detected by the fluoroscopic image. In the present embodiment, the display control unit 140 may cause the display device 190 to display the frame of the tomographic image and the frame of the fluoroscopic image corresponding to the first position of the blood vessel or may cause the display device 190 to display the frame of the tomographic image and the frame of the fluoroscopic image corresponding to the second position of the blood vessel. In addition, the display control unit 140 may cause the display device 190 to display the frame of the tomographic image and the frame of the fluoroscopic image corresponding to the first position of the blood vessel, and the frame of the tomographic image and the frame of the fluoroscopic image corresponding to the second position of the blood vessel.

According to the present embodiment described above, the vascular length at the position designated in the fluoroscopic image can be easy to know. In the present embodiment, the fluoroscopic image and the tomographic image corresponding to the position designated in the fluoroscopic image are displayed together with the vascular length. However, displaying thereof may be independently performed. For example, when the user inputs instructions indicating that the vascular length is to be displayed, after displaying the fluoroscopic image and the tomographic image corresponding to the two positions designated in the fluoroscopic image, the vascular size corresponding to the position may be calculated and displayed.

In the present embodiment, the vascular length at the designated position is displayed. However, the information to be displayed is not limited thereto. For example, in addition to displaying the vascular length, or instead of displaying the vascular length, the display device 190 may display the longitudinal cross-sectional image from the first position of the blood vessel to the second position of the blood vessel. In addition, displaying of the transverse cross-sectional image can be omitted when the longitudinal cross-sectional image is displayed.

Each of the embodiments described above can also be realized by causing a computer to execute a computer program. In other words, a computer program which realizes the function of each of the units according to each of the embodiments described above is supplied to a system or a device which includes the computer via a network, a storage medium, or the like. Then, each of the embodiments described above can be realized by causing the computer including a processor and a memory to read the computer program through the memory and causing the processor to operate in accordance with the computer program on the memory. The program can be stored on a tangible, non-transitory computer readable storage medium, such as a memory, a hard disk, a CD-ROM, and the like.

The detailed description above describes an information processing device, an imaging system, an information processing method, and a program. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An information processing device comprising:
   image collecting means for collecting vascular tomographic images which are taken by a probe inserted into a blood vessel and are configured to include a plurality of frames, and vascular fluoroscopic images which are taken while the probe is inserted into the blood vessel and are configured to include a plurality of frames;
   position identifying means for identifying a position of an image of the probe in each of the frames of the fluoroscopic images;
   display controlling means for causing a display to display the frame of the fluoroscopic image at the same time as the frame of the tomographic image which is taken at substantially the same time as the frame of the fluoroscopic image; and
   designation acquiring means for acquiring information of a position of a blood vessel designated by a user from the frame of the fluoroscopic image which is displayed by the display,
   wherein the display controlling means causes the display to display the frame of the fluoroscopic image including the image of the probe at a position closest to the position of the blood vessel designated by the user at the same time as the frame of the tomographic image which is taken at substantially the same time as the frame of the fluoroscopic image, and
   wherein the display controlling means causes the frame of the fluoroscopic image including the image of the probe at the position closest to the position of the blood vessel designated by the user to be displayed when a distance between the position of the image of the probe included in the frame of the fluoroscopic image and the position of the blood vessel designated by the user is equal to or less than a predetermined threshold value.

2. The information processing device according to claim 1,
   wherein the position identifying means identifies the position of the image of the probe by detecting the image of the probe from each of the frames of the fluoroscopic images.

3. The information processing device according to claim 1, further comprising:
   correspondence acquiring means for acquiring information indicating the frame of the tomographic image which is taken at substantially the same time as the frame of the fluoroscopic image regarding each of the frames of the fluoroscopic images.

4. The information processing device according to claim 1,
   wherein the display controlling means causes the display to display information indicating the position of the image of the probe included in the frame of the fluoroscopic image in addition to the frame of the fluoroscopic image.

5. The information processing device according to claim 1, further comprising:
   vascular information acquiring means for acquiring vascular information of the blood vessel,
   wherein the display controlling means causes the display to display the vascular information.

6. The information processing device according to claim 5,
   wherein the vascular information acquiring means acquires a vascular diameter with reference to the frame of the tomographic image at the position of the blood vessel by the user as the vascular information.

7. The information processing device according to claim 5,
   wherein the vascular information acquiring means acquires a vascular length between two positions in the blood vessel designated by the user as the vascular information.

8. The information processing device according to claim 3,
   wherein the correspondence acquisition unit acquires a correspondence relationship in accordance with a geometric feature detected from the fluoroscopic image and a geometric feature detected from the tomographic image.

9. The information processing device according to claim 1,
   wherein the tomographic images and the vascular fluoroscopic images having a plurality of frames are grouped by cardiac cycle into at least two groups having at least one frame, and the display control unit is configured to select one of the groups.

10. An information processing device comprising:
    image collecting means for collecting vascular tomographic images which are taken by a probe inserted into a blood vessel and are configured to include a plurality of frames, and vascular fluoroscopic images which are taken while the probe is inserted into the blood vessel and are configured to include a plurality of frames;
    position identifying means for identifying a position of an image of the probe in each of the frames of the fluoroscopic images;
    display controlling means for causing a display to display the frame of the fluoroscopic image at the same time as the frame of the tomographic image which is taken at substantially the same time as the frame of the fluoroscopic image; and
    designation acquiring means for acquiring information of a position of a blood vessel designated by a user from the frame of the fluoroscopic image which is displayed by the display,
    wherein the display controlling means causes the display to display the frame of the fluoroscopic image including the image of the probe at a position closest to the position of the blood vessel designated by the user at the same time as the frame of the tomographic image which is taken at substantially the same time as the frame of the fluoroscopic image, and wherein the position identifying means convert coordinates in the fluoroscopic image designated by the user into relative coordinates with respect to a vascular image.

11. The information processing device according to claim 10, wherein the position identifying means identifies the position of the image of the probe by detecting the image of the probe from each of the frames of the fluoroscopic images.

12. The information processing device according to claim 10, further comprising:

correspondence acquiring means for acquiring information indicating the frame of the tomographic image which is taken at substantially the same time as the frame of the fluoroscopic image regarding each of the frames of the fluoroscopic images.

13. The information processing device according to claim 10, wherein the display controlling means causes the display to display information indicating the position of the image of the probe included in the frame of the fluoroscopic image in addition to the frame of the fluoroscopic image.

14. The information processing device according to claim 10, further comprising:

vascular information acquiring means for acquiring vascular information of the blood vessel, wherein the display controlling means causes the display to display the vascular information.

15. The information processing device according to claim 14, wherein the vascular information acquiring means acquires a vascular diameter with reference to the frame of the tomographic image at the position of the blood vessel by the user as the vascular information.

16. The information processing device according to claim 14, wherein the vascular information acquiring means acquires a vascular length between two positions in the blood vessel designated by the user as the vascular information.

17. The information processing device according to claim 12, wherein the correspondence acquisition unit acquires a correspondence relationship in accordance with a geometric feature detected from the fluoroscopic image and a geometric feature detected from the tomographic image.

18. The information processing device according to claim 10, wherein the tomographic images and the vascular fluoroscopic images having a plurality of frames are grouped by cardiac cycle into at least two groups having at least one frame, and the display control unit is configured to select one of the groups.

* * * * *